US00PP08288P

United States Patent [19]

Trees

[11] Patent Number: Plant 8,288

[45] Date of Patent: Jun. 29, 1993

[54] GERANIUM PLANT — BSR-233 BRIGHT CORAL CULTIVAR

[75] Inventor: Scott C. Trees, Arroyo Grande, Calif.

[73] Assignee: George J. Ball, Inc., West Chicago, Ill.

[21] Appl. No.: 761,707

[22] Filed: Sep. 18, 1991

[51] Int. Cl.[5] ..... A01H 5/00

[52] U.S. Cl. ..... Plt./87.12

[58] Field of Search ..... Plt./87.12

*Primary Examiner*—James R. Feyrer
*Assistant Examiner*—E. F. McElwain
*Attorney, Agent, or Firm*—Burns, Doane, Swecker & Mathis

[57] ABSTRACT

A new and distinct tetraploid *Pelargonium*×*hortorum* cultivar named BSR-233 Bright Coral is provided. This new Zonal Geranium cultivar was the result of a controlled breeding program wherein an unnamed plant designated 7-GRT-1A was pollinated by the Tango cultivar (U.S. Plant Pat. No. 5,933). The new cultivar forms attractive semi-double coral florets and forms dark green non-zoned leaves. Exceptionally good garden performance is exhibited including tolerance to wind and rain. The growth habit is inherently compact with basal self-branching and does not require the use of growth regulators to maintain such growth characteristic.

1 Drawing Sheet

SUMMARY OF THE INVENTION

The present invention comprises a new and distinct Geranium cultivar, botanically known as *Pelargonium*-×*hortorum*, and hereinafter is referred to by the cultivar name BSR-233 Bright Coral.

The new cultivar is the product of a planned breeding program which had as its objective the creation of a highly productive new Geranium cultivar which exhibits attractive blossoms, dark green foliage, a compact self-branching growth habit, no requirement for the use of a growth regulator, and a propensity for rapid rooting. This objective was satisfactorily fulfilled in the cultivar of the present invention.

The breeding program which resulted in the production of the new cultivar of the present invention was carried out in a controlled environment during 1989 at Santa Maria, Calif., U.S.A. The female parent (i.e., the seed parent) was an unnamed plant designated 7-GRT-1A. Such female parent formed semi-double florets, and medium green foliage without zoning. The male parent (i.e., the pollen parent) was the Tango cultivar (U.S. Plant Pat. No. 5,933). Such male parent formed semi-double red florets, and formed dark green foliage. The parentage of the new cultivar can be summarized as follows:

7-GRT-1A×TANGO.

The seeds resulting from the above pollination were sown and plantlets were obtained which were physically and biologically different from each other. Selective study which was finalized on Jan. 20, 1990, at Santa Maria, Calif. resulted in the identification of a single plant of the new cultivar. This plant initially was designated BSR-233.

It was found that the new cultivar of the present invention:

(a) exhibits attractive coral semi-double florets,
(b) forms attractive dark green foliage having non-zoned leaves, (c) exhibits good field performance including tolerance to wind and rain, and
(d) exhibits an inherently compact and basal self-branching growth habit in the absence of growth regulators.

Asexual reproduction of the new cultivar by vegetative cuttings initially taken on Feb. 10, 1990, and horticulturally examined in a controlled environment on Apr. 15, 1990, at Santa Maria, Calif., has demonstrated that the characteristics of the new cultivar as herein described are firmly fixed and are retained through successive generations of asexual propagation.

When plant material of the BSR-233 Bright Coral cultivar is subjected to standard random amplified polymorphic DNA marker analysis (RAPD) using polymerase chain reaction (PCR) and a known unique set of DNA primers, it is found to exhibit a distinctive fingerprint map which is on file at the Ball Flora Plant Division of George J. Ball, Inc. at Arroyo Grande, Calif.

BSR-233 Bright Coral has not been observed under all possible environmental conditions to date. Accordingly, it is possible that the phenotype may vary somewhat with variations in the environment, such as temperature, light intensity, and day length.

When the new cultivar of the present invention is compared to the Atlantis cultivar (U.S. Plant Patent pending), the BSR-233 Bright Coral cultivar exhibits a lighter blossom coloration, and forms corolla having a smaller diameter as specified in greater detail hereafter.

The new cultivar of the present invention is being marketed under the Showcase trademark.

BRIEF DESCRIPTION OF THE PHOTOGRAPH

The accompanying photograph shows as nearly true as it is reasonably possible to make the same in a color illustration of this character, a typical specimen of an overall plant of the new cultivar. The plant was grown in a greenhouse at Santa Maria, Calif.

DETAILED DESCRIPTION

The chart used in the identification of colors described herein is The R.H.S. Colour Chart of The Royal Horticultural Society, London, England. Color terminology in common terms sometimes precedes the reference to The R.H.S. Colour Chart information. The color values were determined on Jul. 3, 1991 at 11:00 a.m. to 12:00 noon using a light intensity of 1600 foot-candles at Santa Maria, Calif. The plants described were grown under standard greenhouse conditions.

Classification:

*Botanical.*—*Pelargonium* × *hortorum,* cv. BSR-233 Bright Coral.

*Commercial.*—Zonal Geranium.

INFLORESCENCE

A. Umbel: Umbrella shaped (not round).

*Average diameter.*—Approxmately 11 to 13 cm.

*Average depth.*—Approximately 6 to 7 cm.

*Peduncle length.*—Approximately 17 to 21 cm.

*Peduncle color.*—At base Green Group 140B. The same coloration is exhibited by the Atlantis cultivar. The peduncle of the BSR-233 Bright Coral cultivar is of a distinctly lighter green coloration than that of the Atlantis cultivar which exhibits a dark reddish-green coloration.

*Pedicel length.*—Approximately 3 to 4 cm. When grown in a 4 inch pot at 12 weeks after the sticking of a bare root cutting, the BSR-233 Bright Coral cultivar commonly possesses approximately 5.1 umbels per plant on average, and the Atlantis cultivar commonly possesses approximately 4.2 umbels per plant on average. When five month old plants are grown in the field, the BSR-233 Bright Coral cultivar commonly possesses approximately 35 to 40 umbels per plant while the Atlantis culivar commonly possesses approximately 20 to 25 umbels per plant. Such field grown plants commonly possess approximately 15 to 20 florets per umbel for the BSR-233 Bright Coral cultivar and approximately 18 to 25 florets per umbel for the Atlantis cultivar.

B. Corolla:

*Average diameter.*—Approximately 4.3 to 4.5 cm. This can be compared to approximately 4.7 to 5.0 cm. for the Atlantis cultivar.

*Form.*—Semi-double, commonly 5 petals plus approximately 3 to 4 petaloids. The florets of the BSR-233 Bright Coral cultivar commonly possess non-imbricate outer petals which measure approximately 2.7 cm. in length and approximately 1.9 cm. in width, and smaller inner petaloids which commonly measure in length from approximately 0.2 to 2.4 cm. In contrast the florets of the Atlantis cultivar commonly possess approximately 3 to 4 bottom outer petals which measure approximately 2.3 cm. in length and approximately 2 cm. in width, approximately 2 upper outer petals which commonly are approximately 2.6 cm. in length and approximately 1.7 cm. in width, and approximately 3 smaller inner petaloids which range in length from approximately 1 to 1.8 cm.

*Color (general tonality from a distance of 3 meters)*-.—Coral, Red Group 50A.

*Color (abaxial).*—Coral, Red Group 50A. This compares to Red Group 46C for the Atlantis cultivar.

*Color (adaxial).*—Light coral, Red Group 48B with white at the petal mid-point. This compares to Red Group 50A for the Atlantis cultivar.

C. Bud:

*Shape.*—Upright, in a hemispheroidal cluster.

*Color (abaxial).*—Red, Red Group 45A.

*Color (adaxial).*—Predominantly white, White Group 155A, with red, Red Group 45A at the edge of the petals.

D. Reproductive organs:

*Androecium.*—The anthers commonly are approximately 2 to 3 mm. in length. The pollen is orange in coloration, Orange Group 28A; the filaments commonly are irregular in shape and length; and some filaments are petaloid.

*Gynoecium.*—The pistil length commonly is approximately 8 to 9 mm. on florets which have been open for five days, there is a single stigma which commonly branches into 5 or 6 parts, and the style length is approximately 4.0 to 4.5 mm. on florets which have been open for five days.

*Fertility.*—Commonly does not produce fruits in the absence of mechanical fertilization.

E. Spring flowering response period: Approximately 6 to 7 weeks from rooted cuttings under greenhouse conditions maintained at 55° F. at night and 72° F. during the day when potted on March 1st in a soil mix (e.g., Sunshine No. 2 brand soil mix) in 10 cm. pots.

F. Outdoor flower production: Exceptionally good garden performance with continuous flowering.

G. Durability: Stable chlorophyll upon the shipment of cuttings.

PLANT

A. Foliage: Dark green with no zone.

*Form.*—Reniform, cordate base.

*Margin.*—Slightly crenate.

*Color (abaxial).*—Dark green, Green Group 131C. This compares to a coloration of Green Group 132A for the Atlantis cultivar.

*Color (adaxial).*—Green Group 132C. This compares to a coloration of Green Group 135B for the Atlantis cultivar.

*Susceptibility to Botrytis blight.*—Some tolerance.

B. General appearance and form:

*Internode length.*—Commonly varies from approximately 2 to 3 cm.

*Branching pattern.*—Freely basal branching. No pinching is required to obtain such self-branching.

*Height.*—Approximately 20 to 25 cm. above a 10 cm. pot when the blossoms first open.

I claim:

1. A new and distinct cultivar of Geranium plant named BSR-233 Bright Coral, substantially as herein shown and described, which:

(a) exhibits attractive coral semi-double florets, (b) forms attractive dark green foliage having non-zoned leaves, (c) exhibits good field performance including tolerance to wind and rain, and (d) exhibits an inherently compact and basal self-branching growth habit in the absence of growth regulators.

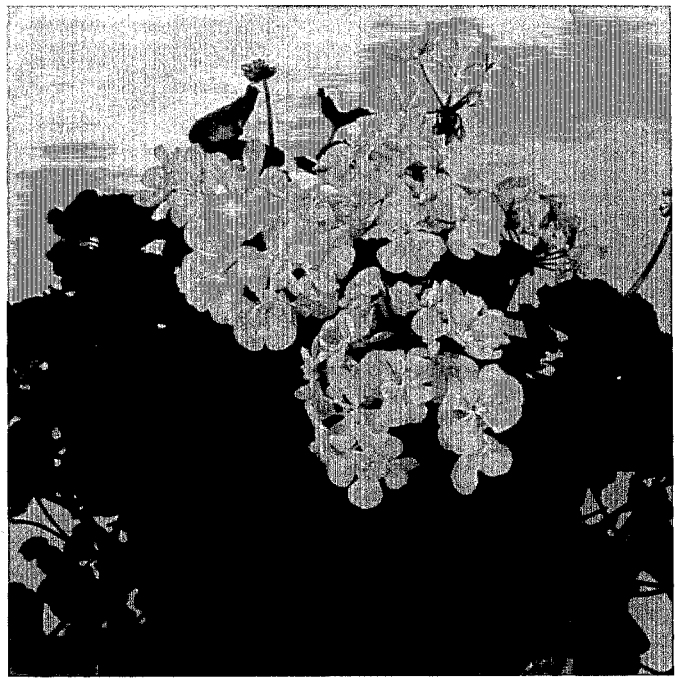

* * * * *